United States Patent [19]

Millstein et al.

[11] Patent Number: 4,786,254

[45] Date of Patent: Nov. 22, 1988

[54] METHOD OF PERMANENTLY RECORDING OCCLUSAL CONTACTS

[76] Inventors: Philip L. Millstein, 15 Langdon St., Cambridge, Mass. 02138; Paul Goldberg, 12 Crocker Cir., West Newton, Mass. 02165

[21] Appl. No.: 139,949

[22] Filed: Dec. 31, 1987

Related U.S. Application Data

[63] Continuation of Ser. No. 829,780, Feb. 14, 1986, abandoned, which is a continuation-in-part of Ser. No. 715,906, Mar. 25, 1985, abandoned.

[51] Int. Cl.$^4$ ................................................ A61C 9/00
[52] U.S. Cl. ...................................................... 433/71
[58] Field of Search .............................. 433/69, 70, 71

[56] References Cited

U.S. PATENT DOCUMENTS

| 1,840,703 | 1/1932 | Cunningham | 433/71 |
| 4,324,567 | 4/1982 | Arcan | 433/71 |
| 4,526,179 | 7/1985 | Szlesky | 28/776 |

*Primary Examiner*—Robert Peshock
*Attorney, Agent, or Firm*—Wolf, Greenfield & Sacks

[57] ABSTRACT

An impression film, adapted to intraorally record an occlusal position at virtually unaltered vertical and horizontal dimensions, is matched to a light source and a photographic film such that micron changes in the thickness of the impression film can result in photographically measurable changes in the percent transmission of light from the light source through the impression film. In this manner, an occlusal position can be permanently documented.

2 Claims, No Drawings

METHOD OF PERMANENTLY RECORDING OCCLUSAL CONTACTS

RELATED APPLICATIONS

This application is a continuation of application Ser. No. 829,780, filed Feb. 14, 1986 and now abandoned which is a continuation-in-part of Ser. No. 715,906, filed Mar. 25, 1985 and now abandoned.

BACKGROUND OF THE INVENTION

This invention provides a means in dentistry to permanently record the various occlusal positions that occur when opposing teeth are brought together to make contact.

An occlusal position is formed when the surfaces of opposing teeth are brought together to make contact with one another. It is composed of occlusal contacts, near occlusal contacts, and non-contacts. An occlusal contact occurs with the touching of opposing teeth. Near occlusal and non-contacts are those spacial areas that are formed between opposing tooth surfaces that do not touch on closure. Dentists currently lack a reliable recording system for permanently recording the three components of an occlusal position.

A permanent record of an occlusal position would be useful in the diagnosis and treatment of various dental problems, as for example, diagnosis and treatment planning in periodontics, orthodontics and restorative dentistry. Such records could also be valuable for defending against the rising tide of assertions of dental malpractice, or for establishing malpractice. Other uses include (1) clinical diagnosis and longitudinal research, (2) identification procedures (no two recordings other than for the same person are alike), (3) temporomandibular joint determinations, and (4) dental laboratory communication such as in the fabrication of dental bridges and prosthetic replacements.

At present dentists evaluate occlusal positions using occlusal contact indicating media such as articulating paper, typewriter ribbon and articulating film. Patients close their teeth onto the indicating media which leaves marks on the teeth relating to the points of contact. The marks made in situ are then interpreted intraorally.

This technique has several drawbacks. Most significant, the markings produced are intended to be viewed intraorally at the time of the procedure. There is no provision for permanently recording the marks. Also, any mark transferred to the marking indicator itself cannot be permanently recorded; nor can the indicator itself be hygienically stored. A further drawback is that the markings produced do not always represent the actual pattern of contact points but are rather a by-product of the indicator used. There exists a wide range of variability between the occlusal contact markings produced by various indicators, all of which are used for the same purpose—to locate and define occlusal contacts. The indicators may alter the vertical dimension of occlusion which results in a pattern of contacts that differs from the pattern of contacts at an unaltered vertical dimension. This problem is exacerbated by the natural movement of the jaw. As the two rows of teeth are brought together, the back teeth may approach contact before the front teeth. Conventional indicators may act as a wedge between the two rows, preventing the teeth from reaching their normal occlusal position. This produces a false pattern of contacts. These indicators may also be forced between the teeth, thereby altering the horizontal dimension of occlusion, which results in a false pattern of contacts. Finally, these indicators are not capable of distinguishing between near contacts and non-contacts.

A variety of wax strips are currently in use to evaluate occlusal positions. Unlike indicating media such as typewriter ribbon, the markings produced by biting into the wax strips are intended to be viewed extraorally by visual inspection. Again, these wax strips are not intended for or capable of providing a hygienic permanent record of an occlusal position. These wax strips also do not provide any quantitative information about near contacts. Rough visual inspection does not allow for discriminating subtle differences between multiple measurements in the same individual before and after treatment or over time. Likewise, rough visual inspection is not sufficiently precise to serve as an identification tool. Finally, the markings produced by an individual vary widely with each product.

A recent advance in the area of analyzing occlusion is the process known as photo-occlusion. In this process, an articulating film is placed in the patient's mouth. Bringing opposing teeth together impresses a strain pattern in the "wafer." This strain pattern is caused by permanent local deformations of the wafer. After removing the wafer from the patient's mouth, the wafer is viewed on an expensive optical instrument. A strain pattern appears in colors with each color corresponding to a different strain intensity. This strain color phenomenon is due to the residual birefringence resulting from the permanent local deformations of the wafer. The strain pattern may then be permanently recorded by photographing the strain pattern.

While this system is an advance in the field of occlusion analysis, it fails to solve many of the problems of the prior art. First, photo-occlusion measures strain. In particular, it measures the forces which exist between opposed teeth as the two rows of teeth are closed upon the wafer. While such a measure may be correlated with occlusal contacts or the distance between teeth at near contact areas, it is at best just that, a correlation and does not accurately record the actual contact and near contact points. Second, the wafer alters the vertical dimension at closure due to its thickness and false markings will occur. Third, because the wafer offers resistance to closure, duplicate bite impressions may yield different results due to any variation in bite pressure. Furthermore, overcoming this resistance to closure may alter the horizontal dimension of the bite further producing a pattern that does not represent the actual or near occlusal contacts. Duplicating bite impressions against this resistance is particularly problematic where the measurements of young or feeble persons (or even deceased persons for identification purposes) are attempted. Finally, while this system offers one of the first methods for conveniently producing a permanent hygienic record of an occlusal position, it does so only at a substantial cost since expensive polariscopic equipment is required.

The applicant's invention overcomes these and other shortcomings.

It is an object of the invention to provide a system for examining an occlusal position at virtually an unaltered vertical dimension.

It is also an object of the invention to provide a system for examining an occlusal position at virtually an unaltered horizontal dimension.

It is a further object of the invention to provide a means for permanently documenting an occlusal position.

It is a further object of the invention to provide a means for permanently documenting an occlusal position at a relatively insubstantial expense.

It is a further object of the invention to provide a means for computerized analysis of an occlusal position.

SUMMARY OF THE INVENTION

According to the invention, an impression film, adapted to intraorally record an occlusal position at virtually unaltered vertical and horizontal dimensions, is matched to a light source and a photographic film such that micron changes in the thickness of the impression film can result in photographically measurable changes in the percent transmission of light from the light source through the impression film. In this manner, an occlusal position can be permanently documented.

Also according to the invention, a method for permanently documenting an occlusal position is provided. An impression film capable of recording an occlusal position at virtually unaltered vertical and horizontal dimensions is placed intraorally. The impression film is matched to a light source and a photographic film such that micron changes in the thickness of the impression film can result in photographically measurable changes in the percent transmission of light from the light source through the impression film. The patient then makes a bite impression into the impression film. Subsequently the impression film is removed from the patient's mouth and a photographic representation of the impression film is made.

These and other features of this invention will be better understood and appreciated by the following detailed description.

DETAILED DESCRIPTION

The occlusal impression film of the present invention is the articulating medium from which the permanent record of an occlusal position is obtained. The impression film must have flow properties such that it deforms to make a representation of the occlusal position when opposing teeth are brought together upon it. It must plastically deform without significantly altering the vertical and horizontal dimensions of the occlusal position. Thus, it must offer little resistance to closure. The impression film should not, however, wrinkle or bend unfavorably upon use and its properties should not change upon exposure to moisture. The impression film must also be shape retaining at the approximate temperature of the mouth cavity, or approximately 37° C.

Films having the above characteristics have been described in U.S. Pat. No. 3,604,116. Generally, a carrier of strong but pliable sheet material having a thickness of less than 20 microns supports a coating of plastically deformable impression material on at least one of its two faces. The mechanical strength of the carrier material must be much greater than that of the impression material. The carrier must be light transmissive and can be any of a great number of commercially available plastic sheets having a nominal thickness of not more than 15 microns. Preferably the carrier sheet is a 6.5 microns thick DuPont Mylar sheet, commercially available.

The impression materials preferred as coatings on the carrier sheet are wax-based compositions. The wax-based impression materials must adhere adequately to the plastic carrier sheets, but not so strongly that the wax is not displaced by bringing the teeth together upon the impression film without puncturing the carrier sheet. Commercially available adhesives applied in negligible thicknesses between the carrier sheet and the wax-based impression material achieve the desired results.

When an impression of the occlusal position is made, occlusal contact points will appear as areas on the film essentially free of impression material. Near contact points and non-contact points will have a variable appearance depending on the thickness of the impression film. For example, if the impression film is 50 microns thick, spaces between 50–70 microns will not displace any impression material, but will appear as undisturbed areas or ridges of piled up impression material due to the displacement of impression material from surrounding areas. Alternatively, if the impression film is 100 microns thick, spaces between 50 and 70 microns will displace impression material. Preferably, the impression film is just thicker than the largest space defined by a near contact. Thus, near contacts will appear as areas on the film having a thickness of impression material less than the overall thickness of the impression film, but not scraped free. Such areas will, in general, surround actual contact points. It is, of course, likely that some near contact points will occur in areas remote from actual contact points. Preferably, non-contact points will appear as either undisturbed areas on the impression film or ridge areas of piled-up impression material due to the displacement of impression material from actual and near contact points. Thus, after a bite impression, the impression film will in general show actual contact points where essentially all of the impression material has been displaced, surrounded by near contact points where some but not all of the impression material has been displaced, which in turn are surrounded by ridges of piled-up impression material, which in turn re surrounded by undisturbed areas on the impression film.

Impression films having a thickness greater than 200 microns may begin to alter the vertical or horizontal dimension of an occlusal position. It is, however, at least theoretically possible to design an impression material having flow properties that will avoid such alteration. It should be recognized that measurements taken at slight alteration of the vertical or horizontal dimensions can still provide useful information and that impression films thicker than 200 microns may be used for certain purposes.

The present invention resides in creating an impression film having not only the above properties, but also having light absorptive properties such that micron changes in the thickness of the impression film can result in measurable changes in the percent transmission of a particular light source through the impression film. Where conventional photographic techniques are used, the impression material must match both a particular light source and a particular photographic film. Matching may be accomplished in two ways. For clarity, the wavelengths of light emitted by the light source is the emission range, the wavelengths of light absorbed by the impression film is the absorption range, and the wavelengths of light exposing the photographic film is the exposure range. The transmission range, absorption range and exposure range must overlap. If the emission range is equal to or included within the absorption range, then the exposure range may be any range so long as it includes some part of the emission range. Alternatively, if the emission range overlaps with but also falls outside of the absorption range, then the exposure range must include some part of the range common to both the emission range and the absorption range, but must not include that part of the emission range falling outside of the absorption range.

The amount of absorptive material in the impression film, the light intensity and the exposure time will also influence the quality of the permanent record. However, it is most preferable to use a light source and intensity that are available without expensive equipment and an exposure time that will not unduly delay or complicate preparing a permanent record. Selecting the absorptive quality of the impression material then becomes critical. By selecting an absorptive component that absorbs in substantially the same wavelength range emitted by a commonly used light source and by precisely selecting an amount of absorptive component in the impression material, micron changes in the thickness of the impression material can result in differences in the amount of light transmitted, which differences are photographically measurable and visually discernable in the developed photographic film.

A high-speed microdensitometer can be used to convert the photometric data on the film transparency to digitized form for computer processing. A digitized topographic picture may then be produced for analysis and comparison. The computerized record may also be a numerical one, as opposed to a topographic pictorial one.

It should be recognized that other techniques for transferring the information contained on an impression film to a permanent record are possible. For example, certain digital image processing equipment are capable of digitizing directly from object material. It is therefore possible to prepare a digitized topographic picture without first making a record on conventional photographic film.

In practice, the impression film may be held in any of a number of conventional holders. Generally, such holders include a pair of arms which hold the impression film. The arms are far enough apart so that a patient's bite will fall between them and close enough together so that they fit inside the patient's mouth. The patient opens the mouth, separating the two rows of teeth. The impression film is then hygienically placed between the two rows of teeth. The patient then brings the two rows of teeth together to a normal bite position. The two rows of teeth are again separated and the impression film is removed. Once removed, the impression film can be transformed into a permanent record of the occlusal position.

EXAMPLE

The impression material used was Freeman No. 266 Thermo-Stable Sheet Wax purchased from Freeman Mfg. Co., 1246 W. 70th Street, Cleveland, Ohio 44102. It has a melting point of 275°. Its hardness, as measured by ASTM D1321 (penetrometer, ring and ball), is 11 dmm penetration of a ball having 100 gram weight at room temperature, and 39 dmm for 150 grams. Its flow properties were determined by placing a two kilogram weight on a pellet of the wax at 50° centigrade and measuring the height change of the pellet after a dwell time of 10 minutes. The height change was 55%. Its percent transmission is zero below 380 nanometers (UV range) and increases steadily above 380 nanometers.

The wax was purchased in sheets 200 microns thick. The sheets were rolled in a calender to a thickness of 125 microns.

The impression material was then mounted on a board and hand sprayed with a pressure sensitive adhesive, applied at a negligible thickness. The adhesive was Scotch Brand Photomount, Catalog No. 6094, obtained from 3M Company, St. Paul, Minn. Subsequently, the 6.5 microns thick DuPont Mylar polyester film was laid on top of the pressure sensitive adhesive to adhere it to the impression material. This three layer impression film was then cut into approximately 2×3 inch pieces for testing.

The impression film was placed intraorally as described above and a bite impression of an occlusal position was taken. Subsequently, a permanent hygienic record was made of the information contained in the impression film using a conventional box-type contact printer. The film used was KODAK X-OMAT Duplicating Film obtained from Eastman Kodak Company, Rochester, N.Y. 14650. The film consists of photographic emulsion coated on one side of a blue-tinted, polyester base. An antihalation coating and matte surface are on the other side. The film is designed for exposure with a near-ultraviolet black-light source. The light source was a 15-watt BLB ultraviolet fluorescent lamp (F15T8BLB in trade catalogs). This light source transmits in the near-ultraviolet range.

The impression film was placed on the glass top of the box-type contact printer. An unexposed sheet of the KODAK X-OMAT Duplicating Film was then placed on top of the impression film with the emulsion side facing down. The light source was then turned on for one second. The film was subsequently developed in a conventional automatic film processor. The developed film showed a representation of the occlusal position, with differences of as little as 15 microns visually discernable.

It should be understood that the foregoing description of the invention is intended merely as illustrative thereof and that other embodiments and modifications may be apparent to those skilled in the art without departing from its spirit.

Having thus described the invention, what we desire to claim and secure by letters patent is:

1. A method for permanently documenting an occlusal position comprising:
   selecting a light source having an emission range, selecting a photographic film having an exposure range and selecting an impression material having an absorption range wherein the emission range is equal to or included within the absorption range and the exposure range includes some part of the emission range such that micron changes in the thickness of the impression material can result in photographically measurable changes in the percent transmission of light from the light source through the impression material,
   forming an impression film of uniform thickness from said impression material, said impression material having flow properties such that the impression material may be displaced at actual and near-occlusal contacts without altering normal occlusion and without altering the density of the material itself when the teeth are brought together upon the material and said impression material having shape-retaining ability at about body temperature and below, said thickness, flow properties and shape-retaining ability allowing said impression material to intra-orally record an occlusal position at virtually unaltered vertical and horizontal dimensions, placing said impression film intra-orally, then having the patient make a bite impression into the impression film, then removing the impression film from the patient's mouth and, making a photographic representation of the impression film.

2. A method for permanently documenting an occlusal position comprising:

selecting a light source having an emission range, selecting a photographic film having an exposure range and selecting an impression material having an absorption range wherein the emission range overlaps with and falls outside of the absorption range and the exposure range includes a portion of the range common to both the emission range and the absorption range, but does not include any part of the emission range falling outside of the absorption range such that micron changes in the thickness of the impression material can result in photographically measurable changes in the percent transmission of light from the light source through the impression material, forming an impression film of uniform thickness from said impression material, said impression material having flow properties such that the impression material may be displaced at actual and near-occlusal contacts without altering normal occlusion and without altering the density of the material itself when the teeth are brought together upon the material and said impression material having shape-retaining ability at about body temperature and below, said thickness, flow properties and shape-retaining ability allowing said impression material to intra-orally record an occlusal position at virtually unaltered vertical and horizontal dimensions, placing said impression film intra-orally, then having the patient make a bite impression into the impression film, then removing the impression film from the patient's mouth, and making a photographic representation of the impression film.

* * * * *